(12) United States Patent
Shampine et al.

(10) Patent No.: US 7,542,543 B2
(45) Date of Patent: *Jun. 2, 2009

(54) APPARATUS AND METHOD FOR WELL SERVICES FLUID EVALUATION USING X-RAYS

(75) Inventors: Rod Shampine, Houston, TX (US); Joel Groves, Leonia, NJ (US); Anthony Durkowski, Lawrenceville, NJ (US); Etienne Vallee, Princeton, NJ (US); Peter Wraight, Skillman, NJ (US)

(73) Assignee: Schlumberger Technology Corporation, Sugar Land, TX (US)

( * ) Notice: Subject to any disclaimer, the term of this patent is extended or adjusted under 35 U.S.C. 154(b) by 184 days.

This patent is subject to a terminal disclaimer.

(21) Appl. No.: 11/532,236

(22) Filed: Sep. 15, 2006

(65) Prior Publication Data

US 2008/0069301 A1   Mar. 20, 2008

(51) Int. Cl.
*G01N 23/06* (2006.01)
*G01V 5/12* (2006.01)

(52) U.S. Cl. .................... 378/56; 378/53; 250/256; 250/265; 250/267

(58) Field of Classification Search .......... 378/51–56, 378/210; 250/256, 258, 261, 264, 267, 268, 250/269.2, 269.3, 265, 266
See application file for complete search history.

(56) References Cited

U.S. PATENT DOCUMENTS

| | | | |
|---|---|---|---|
| 2,316,239 A * | 4/1943 | Hare ................. | 250/394 |
| 2,898,466 A * | 8/1959 | Lintz et al. ........... | 378/56 |
| 3,060,313 A * | 10/1962 | Ohmart et al. ......... | 250/383 |
| 3,183,351 A * | 5/1965 | White ................ | 378/89 |
| 3,202,822 A * | 8/1965 | Kehler ............... | 250/266 |
| 3,452,192 A * | 6/1969 | Hanken .............. | 250/308 |
| 4,172,223 A | 10/1979 | Ishijima et al. | |
| 4,277,681 A * | 7/1981 | Borken .............. | 378/54 |
| 4,490,609 A | 12/1984 | Chevalier | |
| 5,164,590 A | 11/1992 | Coles et al. | |
| 5,247,559 A | 9/1993 | Ohtsuchi et al. | |

(Continued)

FOREIGN PATENT DOCUMENTS

EP   0696354 B1   4/1994

(Continued)

OTHER PUBLICATIONS

Atkinson, et al., "A New Horizon in Multiphase Flow Measurement," Oilfield Review (Winter 2004/2005), vol. 16, No. 4, Schlumberger, pp. 52-63.

*Primary Examiner*—Edward J Glick
*Assistant Examiner*—Anastasia Midkiff
(74) *Attorney, Agent, or Firm*—Michael Flynn; David Cate; Robin Nava (57) ABSTRACT

A method and apparatus for determining the density and phase fractions of well services fluids is shown including an x-ray generator, a sample cell, and a radiation detector. Radiation is passed through the sample cell and fluid and the attenuated radiation signal is used to evaluate the fluid. In one embodiment, a reference radiation detector measures a filtered radiation signal and controls the acceleration voltage and/or beam current of the x-ray generator using this information. The apparatus may be permanently affixed for long term monitoring or temporarily clamped on to a pipe in production.

23 Claims, 7 Drawing Sheets

U.S. PATENT DOCUMENTS

| | | |
|---|---|---|
| 5,441,340 A | 8/1995 | Cedillo |
| 5,479,020 A | 12/1995 | Mohn |
| 5,591,922 A | 1/1997 | Segeral et al. |
| 5,680,431 A | 10/1997 | Pietras, III et al. |
| 5,689,540 A | 11/1997 | Stephenson et al. |
| 5,742,660 A | 4/1998 | Majewski et al. |
| 5,778,041 A | 7/1998 | Chase et al. |
| 5,854,820 A | 12/1998 | Slijkerman et al. |
| 6,097,786 A | 8/2000 | Groves et al. |
| 6,182,505 B1 | 2/2001 | Segeral |
| 6,265,713 B1 | 7/2001 | Berard et al. |
| 6,286,367 B1 | 9/2001 | Segeral |
| 6,335,959 B1 * | 1/2002 | Lynch et al. ................ 378/45 |
| 6,378,380 B1 | 4/2002 | Kusters et al. |
| 6,389,908 B1 | 5/2002 | Chevalier et al. |
| 6,405,604 B1 | 6/2002 | Berard et al. |
| 6,412,561 B1 | 7/2002 | Brown |
| 6,722,437 B2 | 4/2004 | Vercaemer |
| 6,748,043 B1 | 6/2004 | Dobbs |
| 6,755,086 B2 | 6/2004 | Salamitou et al. |
| 6,776,235 B1 | 8/2004 | England |
| 2003/0106993 A1 | 6/2003 | Chen et al. |
| 2004/0173016 A1 * | 9/2004 | Fayeulle et al. .......... 73/152.31 |
| 2005/0031074 A1 | 2/2005 | Fitzgerald |
| 2005/0163284 A1 | 7/2005 | Inazuru |
| 2006/0067473 A1 | 3/2006 | Eberhard et al. |
| 2006/0072703 A1 | 4/2006 | Naidu et al. |
| 2007/0274443 A1 * | 11/2007 | Groves et al. .................. 378/54 |
| 2007/0291898 A1 * | 12/2007 | Groves et al. .................. 378/51 |

FOREIGN PATENT DOCUMENTS

| | | |
|---|---|---|
| EP | 0612407 B1 | 9/1997 |
| EP | 0896666 B1 | 7/2002 |
| EP | 0684458 B1 | 12/2002 |
| GB | 2289766 A | 11/1995 |
| GB | 2212903 A | 2/1998 |
| JP | 2002055063 | 2/2002 |
| WO | 9310439 A1 | 5/1993 |
| WO | 9425859 A1 | 11/1994 |
| WO | 0125762 A1 | 4/2001 |
| WO | 0196902 A2 | 12/2001 |
| WO | 03019118 A1 | 3/2003 |

\* cited by examiner

APPARATUS AND METHOD FOR WELL SERVICES FLUID EVALUATION USING X-RAYS

BACKGROUND

This disclosure relates to an apparatus and method for evaluating fluids encountered in a well services context using x-rays. More specifically, this disclosure relates to a system for using x-rays to determine the density and phase fractions of a well services fluid such as a fracturing fluid, a cement slurry, a mixture of drilling mud and cuttings, or any other fluid that may be encountered. These measurements are generally taken above ground using an x-ray generator and a measurement radiation detector with the fluid of interest being housed in a pipe. Additionally, a second reference radiation detector may be used that detects a filtered signal from the x-ray generator and controls an accelerating voltage and a beam current of the x-ray generator.

It is common in the recovery of hydrocarbons from subterranean formations to fracture the hydrocarbon-bearing formation to provide flow channels through which the desired fluid can be obtained. In such operations, a fracturing fluid is injected into a wellbore penetrating the subterranean formation and is forced against the formation strata by pressure. The formation strata or rock is forced to crack or fracture, and a proppant is placed in the fracture by movement of a viscous fluid containing proppant into the crack of the rock. The resulting fracture, with proppant in place, provides improved flow of the recoverable fluid, i.e., oil, gas, or water, into the wellbore.

Fracturing fluids often comprise a thickened or gelled aqueous solution which has suspended therein proppant particles that are substantially insoluble in the fluids of the formation. Proppant particles carried by the fracturing fluid remain in the fracture created, thus propping open the fracture when the fracturing pressure is released and the well is put into production. Suitable proppant materials include sands (silicon, ceramic, resin), walnut shells, sintered bauxite, glass beads, salts, or similar materials. The propped fracture provides a larger flow channel to the wellbore through which an increased quantity of hydrocarbons can flow.

In the industry, it is desirable to monitor the quality of the fluid within the system. This includes monitoring the concentration of particulates within the fluid. Current methods for controlling the quality of the addition of particulates include: pre and post-job batch weighing, mechanical metering during the addition of particulates, or radioactive measurements of the fluid slurries during operations.

Batch weighing provides quality control of the cumulative total product used, but does not provide quality control during on the fly operations for pre-engineered programs that vary the rate at which particulates are added during different phases of the injection.

Mechanical metering involves measuring the rate at which the particulate is added and the rate of the fluid prior to addition (clean rate) and then using these rates to calculate the particulate concentration of the slurry. The calculation for concentration is based on the knowledge of the density of the fluid and the particulate material. However, mechanical metering is prone to slippage and inaccuracies due to the efficiencies of the mechanical system being employed. The quality of the measurement is therefore limited.

The density of fracturing fluids has been determined using radioactive systems as well. Specifically, gamma-ray densitometers are currently used in the oilfield for controlling the proppant mass balance in fracturing jobs. The basic measurement is the attenuation of Cesium ($Cs^{137}$) 662 keV gamma-rays by the fracturing fluid. With proper calibration and data processing, the proppant mass balance error is in the range of 1-2%. This type of system takes a single measurement of the radiation flux reaching the detector and determines a density from this measurement.

While this type of system can provide an accurate result, there are drawbacks to the use of a chemical source such as $Cs^{137}$ in measurements in the field. Any radioactive source carries high liability and strict operating requirements. These operational issues with chemical sources have led to a desire to utilize a safer radiation source. Although the chemical sources do introduce some difficulties, they also have some significant advantages. Specifically, the degradation of their output radiation over time is stable allowing them to provide a highly predictable radiation signal. An electrical radiation generator would alleviate some of these concerns, but most electrical photon generators (such as x-ray generators) are subject to issues such as voltage and beam current fluctuation. If these fluctuations can be controlled, this would provide a highly desirable radiation source.

In addition to measuring the density of fracturing fluid, it is also useful to measure properties of other fluids utilized in the oilfield. For instance, when production on a well comes to a close, it is necessary to fill the well with a cement slurry to stabilize the remaining fractures surrounding the well. It is desirable to use the same tool used for fracturing fluid density determination to determine the phase fractions of water and cement in the cement slurry. Prior art systems for phase fraction determination have also utilized chemical sources which may not be desirable for the reasons detailed above.

Accordingly, a need has been identified for a tool that may be used to determine properties of any fluid encountered in the well services context. One specific example is to measure the density of fracturing fluid employing an electrical photon generator such as an x-ray generator. This generator must be stable over time with its parameters closely controlled to ensure accurate measurements regardless of changing conditions. Additionally, it is desired to use the same system to determine the phase fractions of cement and water in a cement slurry or the characteristics of any other well services fluid that may be encountered.

BRIEF SUMMARY OF THE INVENTION

In consequence of the background discussed above, and other factors that are known in the field of fracturing fluid density determination, applicants recognized a need for an apparatus and method for determining properties of fluids collected in a well services environment. Applicants recognized that an x-ray generator with a carefully controlled acceleration voltage and beam current could be used along with one or more radiation detectors to provide a reliable measure of the characteristics of a host of fluids.

One embodiment comprises a method and apparatus for determining the density of a fracturing fluid. In one aspect, an x-ray generator provides radiation input that is attenuated by a fracturing fluid in a pipe. The attenuated radiation is measured and a density of the fracturing fluid is determined. Additionally, the radiation output by the x-ray generator may be filtered to produce a high energy region and a low energy region, this spectrum being introduced to a radiation detector. The output of this radiation detector is used to control the acceleration voltage and beam current of the x-ray generator.

Another embodiment of the present invention allows for the determination of the phase fractions of water and cement in cement slurry. Again, radiation is introduced to a pipe through which the cement slurry is passing; the readings of a radiation detector are used to calculate the phase fractions.

The present invention is useful on any fluid encountered and is not limited to the two specific examples detailed herein.

THE DRAWINGS

The accompanying drawings illustrate embodiments of the present invention and are a part of the specification. Together with the following description, the drawings demonstrate and explain principles of the present invention.

DETAILED DESCRIPTION

Figure 1:
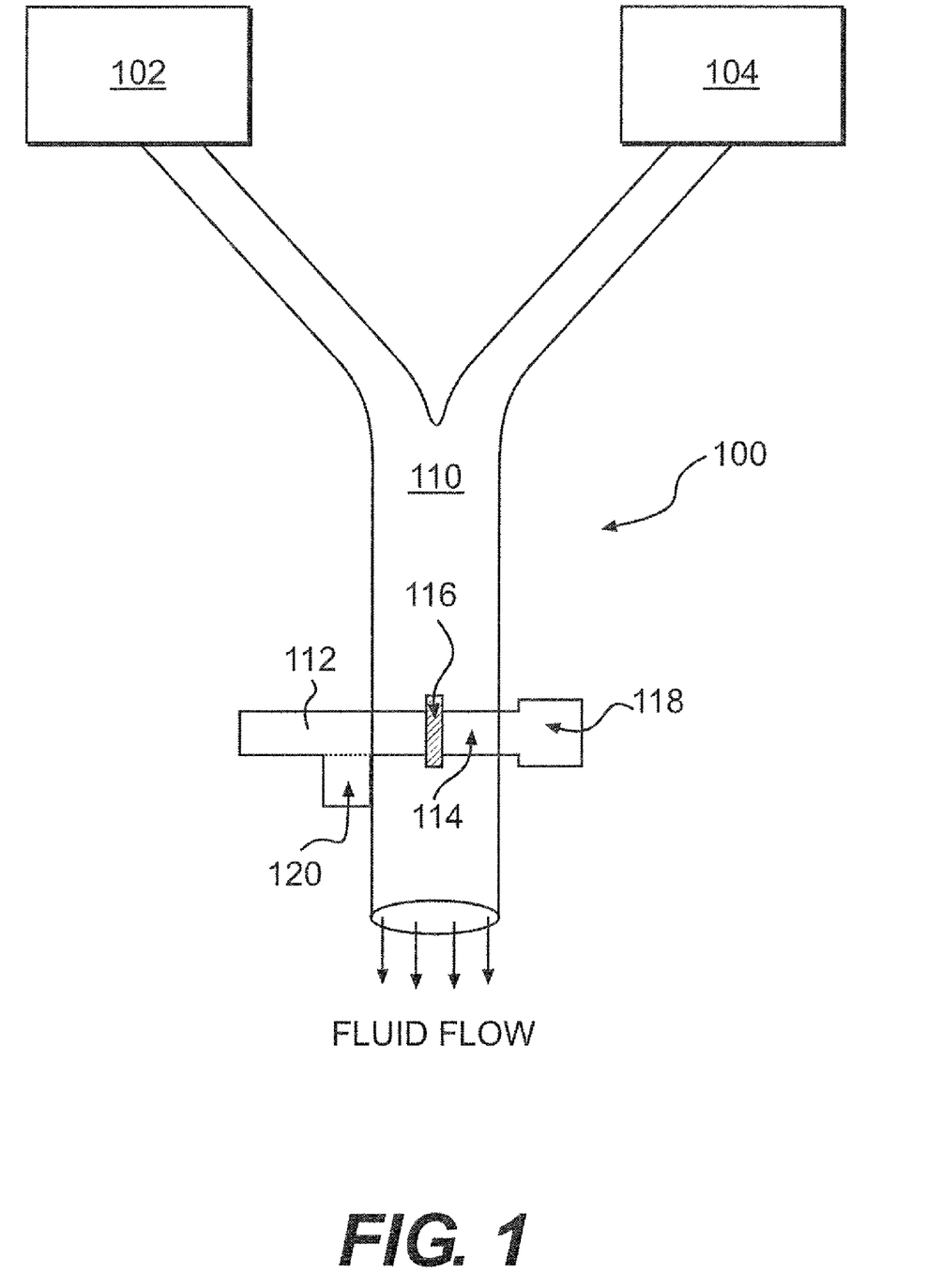
FIG. 1 is a schematic view of the operational context in which the present apparatus and method can be used to advantage.

Referring now to the drawings and particularly to FIG. 1 wherein like numerals indicate like parts, there is shown a schematic illustration of an operational context 100 of the instant invention. This figure shows one example of an application of the invention for determining the density of fracturing fluids. The invention is applicable to any well services fluids and this is being described as one example. As described above, fracturing fluid generally comprises a fluid being mixed with a solid proppant. Proppant source 102 supplies solid material while fluid source 104 provides the fluid base for the fracturing fluid. The proppant and fluid is mixed at point 110 to become fracturing fluid.

In one embodiment, a device for determining the density of the fracturing fluid is clamped on to the pipe. Cuff 114 is connected by the connection mechanism 116. Not pictured is an opposing hinge or other connection mechanism that allows the device to be opened and placed on or removed from the pipe. X-ray generator 112 creates radiation that is passed through the pipe as well as its contents. The resulting radiation signal is measured by measurement radiation detector 118. The radiation output from x-ray generator 112 is measured by reference radiation detector 120. The information from these detectors is then used to determine the density of the fracturing fluid and, if an optional reference radiation detector is used, to control the acceleration voltage and beam current of x-ray generator 112.

Some examples of scenarios in which this invention is advantageous include permanent monitoring, mobile testing, laboratory testing, and artificial lift optimization. Those of ordinary skill in the art will recognize that these are merely examples of possible uses and the above examples are not exhaustive.

X-Ray Physics

X-ray tubes produce x-rays by accelerating electrons into a target via a high positive voltage difference between the target and electron source. The target is sufficiently thick to stop all the incident electrons. In the energy range of interest, the two mechanisms that contribute to the production of x-ray photons in the process of stopping the electrons are X-ray fluorescence and Bremsstrahlung radiation.

X-ray fluorescence radiation is the characteristic x-ray spectrum produced following the ejection of an electron from an atom. Incident electrons with kinetic energies greater than the binding energy of electrons in a target atom can transfer some (Compton Effect) or all (Photoelectric Effect) of the incident kinetic energy to one or more of the bound electrons in the target atoms thereby ejecting the electron from the atom.

If an electron is ejected from the innermost atomic shell (K-Shell), then characteristic K, L, M and other x-rays are produced. K x-rays are given off when an electron is inserted from a higher level shell into the K-Shell and are the most energetic fluorescence radiation given off by an atom. If an electron is ejected from an outer shell (L, M, etc.) then that type of x-ray is generated. In most cases, the L and M x-rays are so low in energy that they cannot penetrate the window of the x-ray tube. In order to eject these K-Shell electrons, an input of more than 80 kV is required in the case of a gold (Au) target due to their binding energy.

Another type of radiation is Bremsstrahlung radiation. This is produced during the deceleration of an electron in a strong electric field. An energetic electron entering a solid target encounters strong electric fields due to the other electrons present in the target. The incident electron is decelerated until it has lost all of its kinetic energy. A continuous photon energy spectrum is produced when summed over many decelerated electrons. The maximum photon energy is equal to the total kinetic energy of the energetic electron. The minimum photon energy in the observed Bremsstrahlung spectrum is that of photons just able to penetrate the window material of the x-ray tube.

The efficiency of converting the kinetic energy of the accelerated electrons into the production of photons is a function of the accelerating voltage. The mean energy per x-ray photon increases as the electron accelerating voltage increases.

A Bremsstrahlung spectrum can be altered using a filter and by changing (1) the composition of the filter, (2) the thickness of the filter, and (3) the operating voltage of the x-ray tube. One embodiment described herein utilizes a single filter to create low and high energy peaks from the same Bremsstrahlung spectrum. Specifically, a filter is used to provide a single spectrum measured by a reference radiation detector with a low energy peak and a high energy peak.

Figure 2:
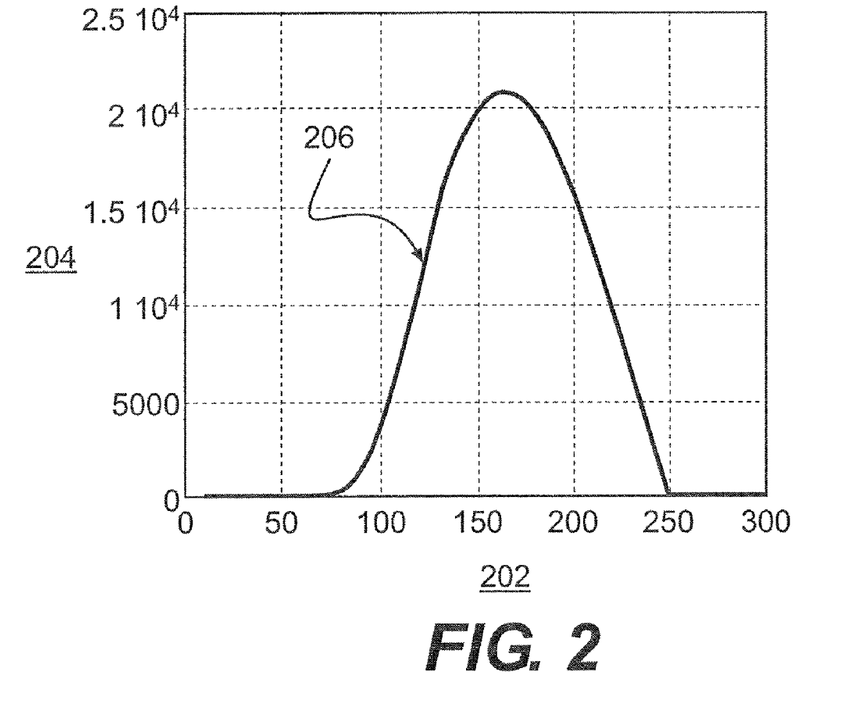
FIG. 2 is a graphic representation of a radiation energy spectrum output by an x-ray generator.

FIG. 2 shows a Bremsstrahlung radiation spectrum 206 that may be employed in the instant invention. Ordinate axis 202 represents energy measured in keV. Abscissa axis 204 is the count rate or the number of photons per second per keV that are incident on a radiation detector. This input radiation is filtered as described above.

Fracturing Fluid Densitometer

One example of a use for the invention in a well services environment is determining the density of a fracturing fluid. The density of a material can be obtained by measuring the attenuation of radiation passed through that material. In addition, if the fluid is a two phase fluid, the same measurement can be used to determine the phase fractions of the fluid. In the instance of most well services fluids, in one embodiment, the radiation must pass through one pipe wall, the fluid, and another pipe wall before being measured by a radiation detector. Due to this, a relatively high energy radiation signal is used. Specifically, the pipes are generally made of steel (largely consisting of iron) which has a mass attenuation coefficient that is nearly independent of energy above 200 keV. Consequently, 200 keV photons penetrate the walls of an iron pipe almost as easily as the 662 keV gamma rays emitted from a Cesium ($^{137}$Cs) or the 1332 keV gamma rays from Cobalt ($^{60}$Co). This benefits the system because the 200 keV signal from an x-ray generator can be more effectively shielded making the system more stable and eliminating the disadvantages of using a chemical radiation source.

Although they provide a number of advantages, unlike chemical sources, all x-ray generators are susceptible to degradation of performance over time. For this reason, in one embodiment, a reference radiation detector is used to control the beam current and acceleration voltage of the x-ray generator.

The density of a material can be determined by analyzing the attenuation of x-rays passed through the material. The initial measurement to be found is not the mass density, $\rho$, that will be the eventual product, but the electron density index, $\rho_e$, of the material. The electron density index is related to the mass density by the definition $$\rho_e = \frac{2 \cdot Z}{A} \rho$$

The attenuation of a beam of x-rays of energy E, intensity $I_0(E)$, passing through a thickness 'd' of material with a density '$\rho_e$' can be written $$I(E) = I_0(E) e^{-\frac{\mu_m(E)\rho_e Ad}{2Z}}$$

where any interaction of the photons traversing the material attenuates the beam. Here, $\mu_m(E)$ is the mass attenuation coefficient of the material. It is important to note that this mass attenuation coefficient is variable depending on the type of fluid that is present. To find the value, calibration testing is often performed or, alternatively, a series of calculations is made based on the known chemistry of the fluid that is present. I(E) in the previous equation does not include the detection of photons created following photoelectric absorption or multiple scattered photons. In the case of most well services fluids, the mass attenuation coefficients of each phase will be known. However, if necessary, these values may be found by calculations or calibration tests using this system.

Figure 3:
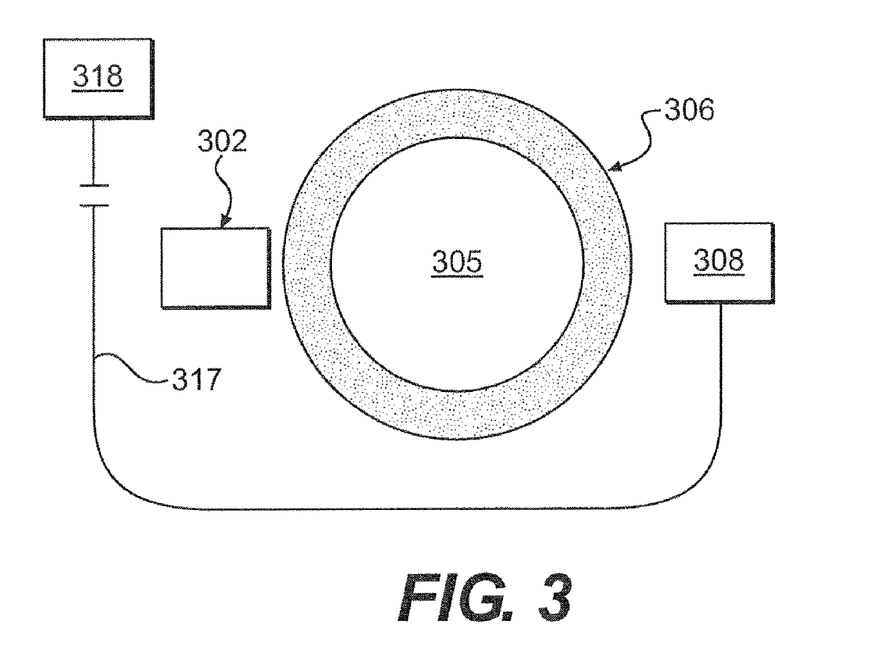
FIG. 3 is a schematic representation of one embodiment of the present invention.

Turning to FIG. 3, one embodiment of the invention is shown. In this embodiment, x-ray generator 302 creates a spectrum like the one shown in FIG. 2. This radiation is passed through one wall of the pipe 306. A well services fluid flows through the inside 305 of the pipe 306. The radiation then passes through the well services fluid and through the opposite wall of pipe 306. The resulting radiation signal is measured by radiation detector 308. The output of radiation detector 308 is then passed along line 317 to analysis unit 318. Analysis unit 318 utilizes the output of radiation detector 308 to determine the density of the well services fluid as detailed below.

Figure 4:
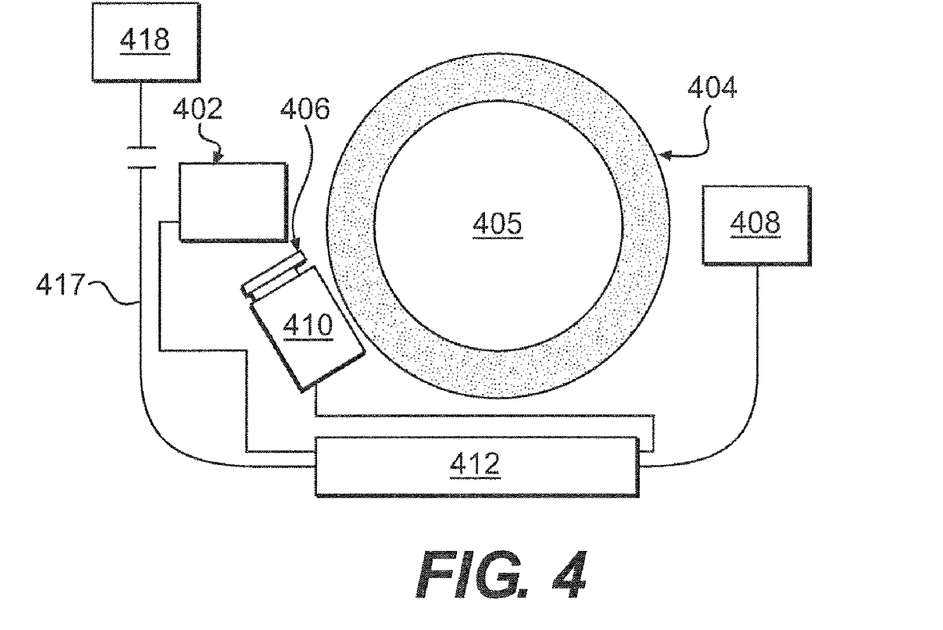
FIG. 4 is a schematic representation of another embodiment of the present invention comprising a reference detector.

FIG. 4 shows another embodiment of the invention. In this embodiment, x-ray generator 402 creates a spectrum like the one shown in FIG. 2. This radiation is passed through one wall of the pipe 404. Well services fluid flows through the inside 405 of the pipe 404. The radiation passes through the well services fluid and through the opposite wall of pipe 404. The resulting radiation signal is measured by measurement radiation detector 408. The output of radiation detector 408 is then optionally passed to an analysis unit 412.

In addition to measurement radiation detector 408, reference radiation detector 410 measures the output of x-ray generator 402 directly. The purpose of this reference detector 410 is to control the beam current and acceleration voltage of x-ray generator 402. Analysis units 412 and 418, connected by line 417, receive the output signals of the radiation detectors and perform the calculations described herein.

In order to correctly control these values, the radiation signal must be filtered by filter mechanism 406. Any high-Z material can be used to filter the input radiation spectrum and produce the dual peak spectrum that is desired. In one embodiment, the filter is gold (Au) and produces the spectrum shown in FIG. 6, other possible materials include, but are not limited to, lead (Pb), tungsten (W), bismuth (Bi), and mercury (Hg). In this figure, Abscissa axis 602 represents energy measured in keV. Ordinate axis 604 is the count rate or the number of photons per second per keV that are incident on a radiation detector. Trace 608 represents a low energy region of the signal, trace 610 represents a high energy region of the signal. The reference radiation detector bins the radiation into two windows, a high energy window with all counts at an energy higher than point 606 and a low energy window with all counts at an energy lower than point 606. The high energy count is referred to as $I_{R_H}$ while the low energy count is referred to as $I_{R_L}$.

Figure 6:
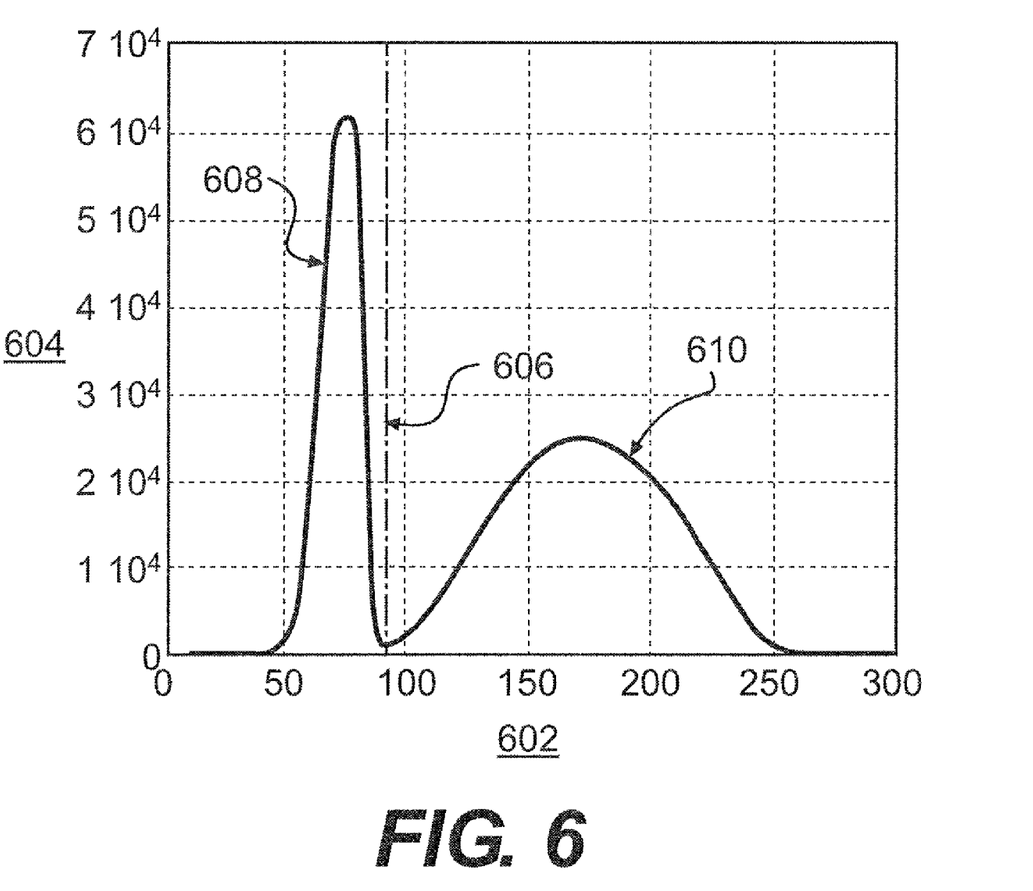
FIG. 6 is a graphic representation of a filtered radiation spectra used in control of an x-ray generator.

As mentioned above, the counts at the reference radiation detector are used to control the acceleration voltage and beam current of x-ray generator 402. This is necessary because any x-ray generator is subject to electrical fluctuations that could cause error in the resultant density calculation. The $I_{R_H}$ and $I_{R_L}$ are both proportional to the number of electrons hitting the target at any given time. Additionally, the ratio of $$\frac{I_{R_H}}{I_{R_L}}$$

is proportional to the acceleration voltage of the x-ray generator $V_{x-ray}$. Looking at FIG. 6, if the voltage of the x-ray generator decreased over time, the spectrum would shift somewhat to the left. This would cause less electrons to be placed in the high energy window and thus the ratio $$\frac{I_{R_H}}{I_{R_L}}$$

would decrease. This embodiment avoids this problem by monitoring this ratio, possibly in unit 412, and altering the acceleration voltage of the x-ray generator 402 to maintain a consistent spectrum.

In addition, it is important to carefully control the beam current output by the x-ray generator. This can also be controlled using the reference detector. The reference detector counts the number of incident photons in the high energy region and low energy region. The output of the reference detector can be used by either monitoring one of these counts or the sum of the two counts. The output of the reference detector is used to control the x-ray generator and ensure a constant beam current.

Figure 5:
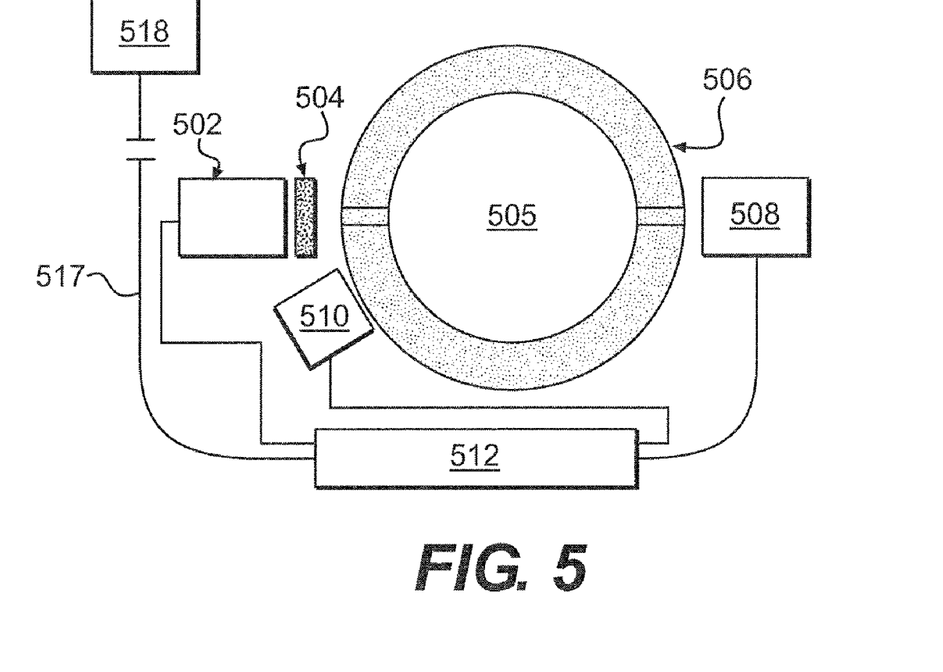
FIG. 5 is a schematic representation of another embodiment of the present invention comprising a reference detector and a window in the wall of the pipe.

Another embodiment using a reference detector is shown in FIG. 5. In this embodiment, a filter 504 is placed at the output of x-ray generator 502 to produce a signal like that shown in FIG. 6. The signal is passed through a window in pipe 506, through the well services fluid on the inside 505 of the pipe 506, and out through another window in pipe 506. The output radiation is measured by measurement radiation detector 508. The filtered radiation signal is also measured by reference radiation detector 510 for controlling the acceleration voltage and beam current of x-ray generator 502 as described above. Analysis units 512 and 518, connected by line 517, receive the output signals of the radiation detectors and perform the calculations described herein. This embodiment is useful when determining the phase fractions of a fluid having three phases. The method for this can be found in U.S. patent application Ser. No. 11/425,285 assigned to Schlumberger Technology Corporation and hereby incorporated by reference as though set forth at length.

Figure 7:
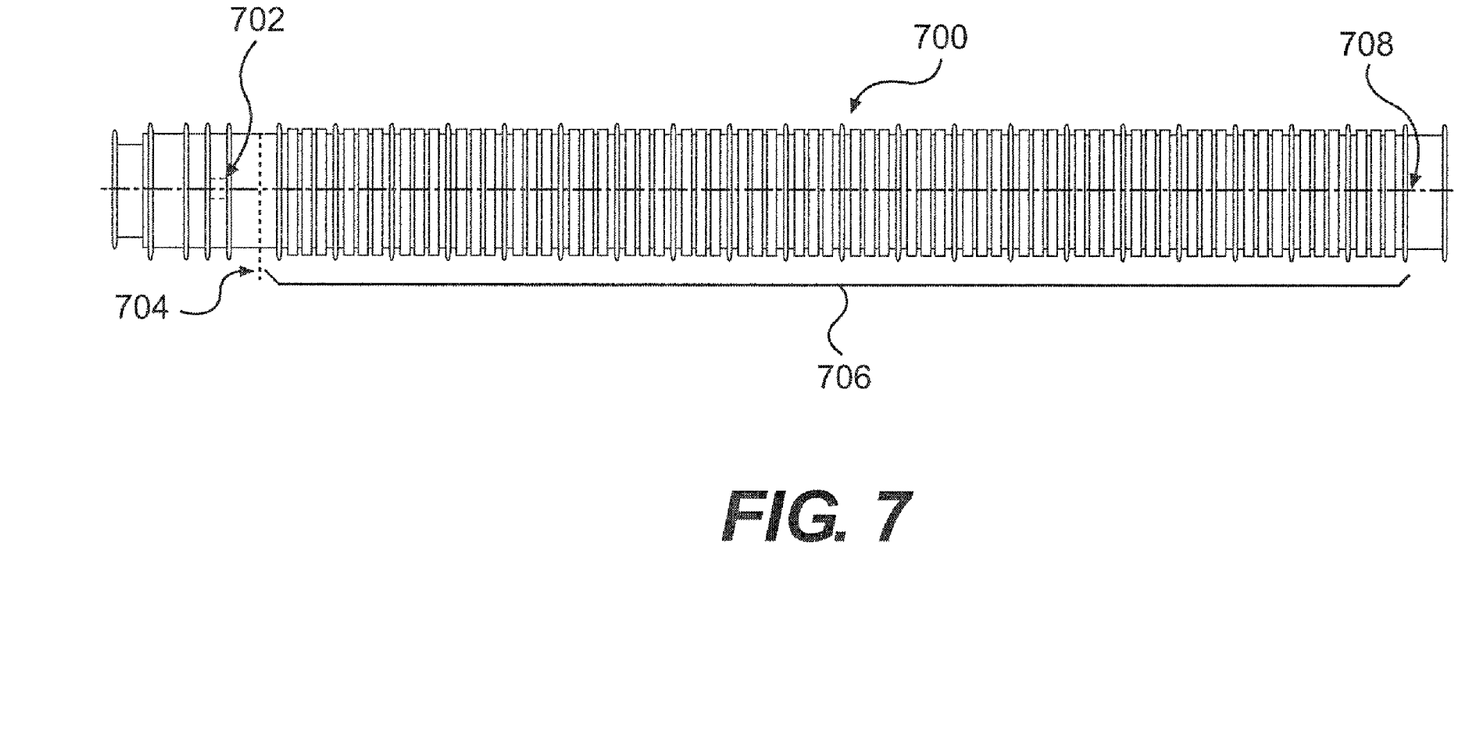
FIG. 7 is a schematic representation of one embodiment of an x-ray tube.

FIG. 7 shows an example of an x-ray tube 700 that may be used. Note that any x-ray tube may be used provided that the acceleration voltage and beam current can be controlled. Element 702 is a cathode that is operable to release electrons in response to exposure to heat. The introduction of a small current heats the cathode 702 and causes it to release electrons. Grid 704 is operable to move electrons released from cathode 702 toward electron accelerating section 706. In one embodiment, this grid 704 is made of Nickel (Ni). Accelerating section 706 speeds electrons toward target 708. In one embodiment, this target is gold (Au.) Upon collision with target 706, tube 700 generates x-rays suitable for use in the instant invention.

Figure 8:
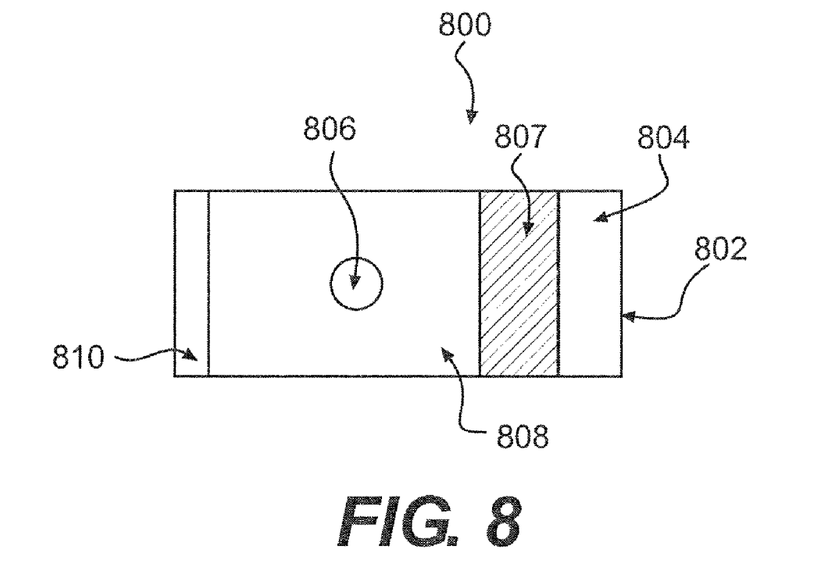
FIG. 8 is a schematic representation of a radiation detector that may be used.

Radiation detectors 308, 408, 410, 508, and 510 may be any type of radiation detector that is capable of monitoring incident radiation and producing an output signal corresponding to that radiation. Generally, the type of radiation detector used comprises a scintillating material interfaced with a photocathode and electron multiplier. One example of a radiation detector that may be used is described in U.S. patent application Ser. No. 09/753,859 assigned to Schlumberger Technology Corporation and herein incorporated by reference as though set forth at length. This radiation detector is illustrated in FIG. 8. Radiation detector 800 comprises an optical window 802 and an attached window housing 804, a primary cylinder 808 having an attached radiation entry window 806, a scintillator crystal 807 and a closing plate 810. The optical window 802 will typically be made of a glass or sapphire plate. The outer housing of the detector will usually be made of a glass sealing alloy such as Kovar. This type of detector is advantageous because it corrects its function with changing temperatures and conditions. This ensures that a constant reading can be obtained in any working environment.

Figure 9:
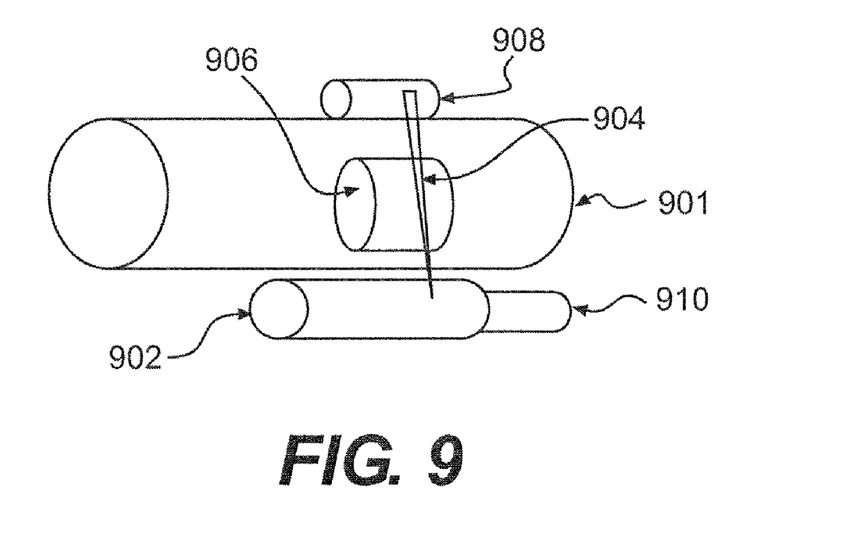
FIG. 9 is a schematic representation of the general structure of one embodiment of the invention.

FIG. 9 shows the general physical layout of the fracturing fluid densitometer. Pipe 901 transports fracturing fluid 906 and may be either a test pipe or a production pipe actively inserting or removing well services fluid into a borehole. X-ray generator 902 emits radiation signal 904 through the first wall of pipe 901, the fracturing fluid, and the second wall of pipe 901. The resulting radiation signal is measured by measurement radiation detector 908. Reference radiation detector 910 measures the output of x-ray generator 910 for controlling its acceleration voltage and beam current as described above.

Figure 10:
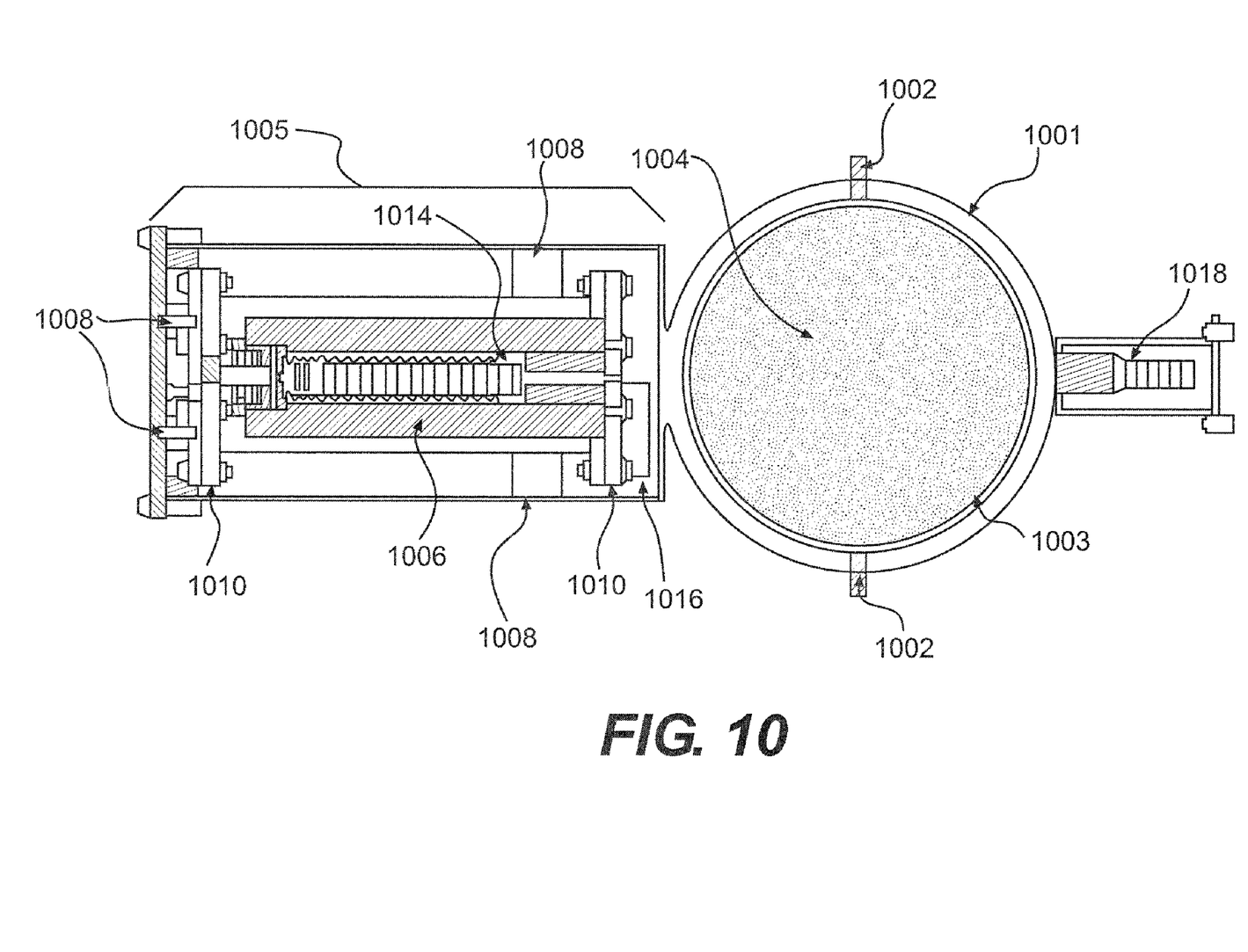
FIG. 10 is a detailed schematic of one embodiment of the invention operable for clamping on to a pipe.

FIG. 10 is a detailed schematic of one embodiment of the invention. Well services fluid 1004 flows through pipe 1003. The invention attaches to pipe 1003 via clamping housing 1001 which is connected at connection mechanism points 1002. In one embodiment, this connection mechanism is a bolt on type that secures the clamp on both sides. X-ray generator 1005 comprises x-ray tube 1006 and associated hardware. Blind flanges 1010 enclose the x-ray tube and ensure that radiation is not released. Shock absorbers 1008 dampen the vibration encountered by the x-ray tube. Tungsten cap 1014 provides shielding. Reference radiation detector 1016 measures the output from x-ray tube 1006 while measurement radiation detector 1018 measures the radiation that has passed through the pipe 1003 and fracturing fluid 1004.

The density of a mixture, $\rho_{mix}$, of two immiscible materials, solid S with density $\rho_S$ and liquid L with density $\rho_L$ is given by $$\rho_{mix} = \rho_S f_S + \rho_L f_L = \rho_S f_S + \rho_L (1 - f_S)$$

Where $f_S$ is the volume fraction $V_S/V_T$, of the solid, and $f_L$ is the volume fraction $V_L/V_T$ of the liquid, where $V_T = V_S + V_L$.

Proppant slurries are specified by the proppant concentration $P_C$, the mass of the solid proppant added to a given volume of the fluid. $P_C$ can be represented by $$P_C = \frac{M_S}{V_L} = \frac{\rho_S \cdot f_S}{1 - f_S}.$$

Using this, the density of the mixture can be written in terms of the proppant concentration $$\rho_{mix} = \frac{\rho_S (P_C + \rho_L)}{P_C + \rho_S}.$$

The standard units for the proppant concentration are pounds of proppant per gallon of fluid while the density is generally expressed in mass per unit volume (gm/ml.) The equation above can be altered to account for these units as follows $$\rho_{mix} = \frac{\rho_S (P_C + 8.34 \rho_L)}{P_C + 8.34 \rho_S}$$

and similarly, $$P_C = \frac{M_S}{V_L} = \frac{8.34 \cdot \rho_S \cdot f_S}{1 - f_S}$$

thus providing the density of the mixture.

Cement Slurry Phase Fraction Determination

Another use for the instant invention is the determination of the phase fraction of a two phase well services fluid. In order to determine the phase fractions of the components of a two phase sample, such as cement slurry, attenuation measurements are taken using the subject invention. The measurement corresponds to the following equation $$I_M = I_M^{(0)} e^{-(\mu_1 d \alpha_1 + \mu_2 d \alpha_2)}$$

where $I_M$ is the number of counts detected by a measurement radiation detector, $I_M^{(0)}$ is the number of counts when the radiation is passed through the empty sample cell, d is the diameter of the sample cell, $\alpha_1$ is the fluid phase fraction of the first fluid constituent such as proppant, and $\alpha_2$ is the fluid phase fraction of the second constituent, such as water. These fractions are unknown and are the subject of interest. This equation can be solved to provide the following $$-\ln\left(\frac{I_M}{I_M^{(0)}}\right) = \mu_1 d\alpha_1 + \mu_2 d\alpha_2.$$

At this point, there is a single equation with two unknowns, so a further equation is needed to solve for the fluid fractions. The sample fluids comprise two phases, so it is also known that $$\alpha_1 + \alpha_2 = 1.$$

Using these two equations, the fluid fractions of the two components making up the well services fluid can be determined based on the radiation passed through the sample.

The phase fraction is especially important in the case of cement slurry where it is necessary to get the correct ratio of water to solid. In some cases, a cement slurry with have a gas injected into it creating a third phase that must be determined. This can be done in one of two ways. The first method is to do as above and first determine the phase fraction of solid and liquid before injecting the gas. Once the gas is injected, the same measurement can be performed knowing that one phase is the solid/liquid mix and the other phase is the gas. This gives the relative amount of each phase and allows for determine of the three phase fractions.

An alternative to this method is to use the configuration shown in FIG. 5. In this configuration, a filtered radiation signal such as that shown in FIG. 6 is sent through the three phase fluid of interest. The measurement radiation detector takes a measurement in the high energy region and the low energy region and bins the resulting radiation into a high energy count and a low energy count. The high energy measurement corresponds to the following equation $$I_{M_H} = I_{M_H}^{(0)} e^{-(\mu_1 d\alpha_1 + \mu_2 d\alpha_2 + \mu_3 d\alpha_3)}$$

where $I_{M_H}$ is the number of high energy counts detected by a measurement radiation detector, $I_{M_H}^{(0)}$ is the number of high energy counts when the radiation is passed through the empty sample cell, d is the diameter of the sample cell, $\alpha_1$ is the fluid phase fraction of a first phase, $\alpha_2$ is the fluid phase fraction of a second phase, and $\alpha_3$ is the fluid phase fraction of a third phase. These fractions are unknown and are the subject of interest. The low energy measurement corresponds to the following equation $$I_{M_L} = I_{M_L}^{(0)} e^{-(\mu_1 d\alpha_1 + \mu_2 d\alpha_2 + \mu_3 d\alpha_3)}$$

where $I_{M_L}$ is the number of low energy counts detected by a measurement radiation detector and $I_{M_L}^{(0)}$ is the number of low energy counts when the radiation is passed through the empty sample cell. Both of these equations can be solved to provide the following $$-\ln\left(\frac{I_{M_H}}{I_{M_H}^{(0)}}\right) = \mu_1 d\alpha_1 + \mu_2 d\alpha_2 + \mu_3 d\alpha_3$$

for the high energy measurement and $$-\ln\left(\frac{I_{M_L}}{I_{M_L}^{(0)}}\right) = \mu_1 d\alpha_1 + \mu_2 d\alpha_2 + \mu_3 d\alpha_3$$

for the low energy signal. Solving for both the high energy and low energy measurements, this provides two equations and three unknowns, so a further equation is needed to solve for the fluid fractions. The sample fluids comprise three phases, so it is also known that $$\alpha_1 + \alpha_2 + \alpha_3 = 1.$$

Using these three equations, the fluid fractions of all three phases can be determined based on the radiation passed through the sample. One example is the phase fractions of water, solid, and gas in a cement slurry.

The application of this invention is not limited to the fluids specifically enumerated above. Any fluid encountered in a well services environment may be evaluated for density and phase fractions using the structures and methods detailed herein. The tool is powerful because it utilizes a safe source of radiation and is highly portable allowing for temporary or permanent testing in the field with a low level of risk.

The preceding description has been presented only to illustrate and describe the invention and some examples of its implementation. It is not intended to be exhaustive or to limit the invention to any precise form disclosed. Many modifications and variations are possible and would be envisioned by one of ordinary skill in the art in light of the above description and drawings.

The various aspects were chosen and described in order to best explain principles of the invention and its practical applications. The preceding description is intended to enable others skilled in the art to best utilize the invention in various embodiments and aspects and with various modifications as are suited to the particular use contemplated. It is intended that the scope of the invention be defined by the following claims; however, it is not intended that any order be presumed by the sequence of steps recited in the method claims unless a specific order is directly recited.

What is claimed:

1. A tool for determining at least one physical property of a well services fluid comprising:
   an x-ray generator;
   an input radiation emitted by said x-ray generator;
   a housing containing a well services fluid;
   an output radiation generated by passing said input radiation through said housing and said well services fluid;
   a measurement radiation detector configured to measure said output radiation and produce a measurement signal;
   a reference radiation generated by altering said input radiation;
   a reference radiation detector being configured to measure the reference radiation and produce a reference signal; and
   an analysis unit, said analysis unit being configured to determine a physical property of said well services fluid using said measurement signal, said analysis unit further being configured to control at least one of an acceleration voltage and a beam current of said x-ray generator using said reference signal.

2. The tool of claim 1, wherein said analysis unit determines said at least one physical property by measuring an attenuation of said input radiation.

3. The tool of claim 1, wherein said analysis unit determines said at least one physical property by comparing said reference signal to said measurement signal.

4. The tool of claim 1, further comprising a filter, wherein said reference radiation is generated by passing said input radiation through said filter.

5. The tool of claim 1, wherein said reference radiation comprises at least one low energy region and at least one high energy region.

6. The tool of claim 5, wherein said acceleration voltage of said x-ray generator is controlled by a ratio of a high energy count to a low energy count detected at said reference radiation detector.

7. The tool of claim 5, wherein said beam current of said x-ray generator is controlled by one of a high energy count, a low energy count, or a sum of a high energy count and low energy count, said high energy count and low energy count being detected at said reference radiation detector.

8. The tool of claim 4, wherein said filter comprises gold (Au).

9. The tool of claim 1, wherein said housing is a well pipe, and wherein said x-ray generator and said measurement radiation detector are removably attached to said well pipe.

10. The tool of claim 1, wherein said well services fluid is a fluid selected from the group consisting of a fracturing fluid and a cement slurry.

11. The tool of claim 10, wherein said at least one property is a property selected from the group consisting of density, and one or more phase fractions.

12. A tool for analysis of a well services fluid comprising:
an x-ray generator;
an input radiation emitted by said x-ray generator;
a housing containing a well services fluid;
an output radiation generated by passing said input radiation through said housing and said well services fluid;
a measurement radiation detector being configured to measure said output radiation and produce a measurement signal;
a reference radiation generated by altering said input radiation;
a reference radiation detector being configured to measure said reference radiation and produce a reference signal;
an analysis unit, said analysis unit being configured to determine at least one physical property of said well services fluid by comparing said reference signal to said measurement signal; and
said analysis unit further being configured to control at least one of an acceleration voltage and a beam current of said x-ray generator using said reference signal.

13. The tool of claim 12, further comprising a filter; wherein said reference radiation is generated by passing said input radiation through said filter.

14. The tool of claim 12, wherein said reference radiation comprises at least one low energy region and at least one high energy region.

15. The tool of claim 14, wherein said acceleration voltage is controlled by a ratio of a high energy count detected at said reference detector to a low energy count detected at said reference detector.

16. The tool of claim 14, wherein said beam current of said x-ray generator is controlled by one of a high energy count, a low energy count, or a sum of a high energy count and a low energy count, said high energy count and said low energy count being detected at said reference radiation detector.

17. The tool of claim 12, wherein said well services fluid is a fracturing fluid comprising a mixture of water and proppant, and wherein said at least one physical property is a density.

18. The tool of claim 12, wherein said well services fluid is a cement slurry, and wherein said at least one physical property is one or more phase fractions.

19. A method for determining a physical property of a well services fluid comprising:
generating an input radiation using an x-ray generator;
passing said input radiation through a well services fluid to produce an output radiation; and
determining at least one physical property by comparing said input radiation to said output radiation,
measuring an attenuation of said input radiation signal;
filtering said input radiation to create a reference radiation wherein said reference radiation comprises at least one low energy region and at least one high energy region;
detecting said reference radiation;
creating a high energy reference count and a low energy reference count; and
controlling an acceleration voltage of said x-ray generator based on a ratio of said high energy reference count to said low energy reference count.

20. The method of 19, further comprising controlling a beam current of said x-ray generator based on one of said low energy reference count, said high energy reference count, and a sum of said low energy reference count and said high energy reference count.

21. The method of claim 19, wherein said method is performed during an oil well operation selected from the group consisting of a fracturing operation and a cementing operation.

22. The method of claim 19, wherein said well services fluid is a fracturing fluid and said at least one physical property is density.

23. The method of claim 19, wherein said well services fluid is a cement slurry and said at least one physical property comprises one or more phase fractions.

* * * * *